US011995234B2

(12) United States Patent
Segal

(10) Patent No.: US 11,995,234 B2
(45) Date of Patent: May 28, 2024

(54) SYSTEMS AND METHODS FOR USING IMAGINED DIRECTIONS TO DEFINE AN ACTION, FUNCTION OR EXECUTION FOR NON-TACTILE DEVICES

(71) Applicant: NAQI LOGIX INC., Vancouver (CA)

(72) Inventor: David Lee Segal, York, PA (US)

(73) Assignee: NAQI LOGIX INC., Vancouver (CA)

( * ) Notice: Subject to any disclaimer, the term of this patent is extended or adjusted under 35 U.S.C. 154(b) by 202 days.

(21) Appl. No.: 17/675,232

(22) Filed: Feb. 18, 2022

(65) Prior Publication Data
US 2022/0171459 A1 Jun. 2, 2022

Related U.S. Application Data

(63) Continuation of application No. 17/073,717, filed on Oct. 19, 2020, now Pat. No. 11,256,330, which is a
(Continued)

(51) Int. Cl.
*G06F 3/01* (2006.01)
*A61B 5/11* (2006.01)
(Continued)

(52) U.S. Cl.
CPC ............ *G06F 3/015* (2013.01); *A61B 5/1128* (2013.01); *A61B 5/245* (2021.01); *A61B 5/316* (2021.01);
(Continued)

(58) Field of Classification Search
CPC ...... G06F 3/015; G06F 16/436; G06F 16/636; G06F 2203/011; A61B 5/1128;
(Continued)

(56) References Cited

U.S. PATENT DOCUMENTS 4,802,103 A * 1/1989 Faggin ............... G06F 18/21
706/30
5,470,081 A 11/1995 Sato et al.
(Continued)

FOREIGN PATENT DOCUMENTS

WO 2011140303 A1 11/2011
WO WO-2014205422 A2 * 12/2014 .............. G06F 3/011

OTHER PUBLICATIONS

Doherty et al, "Improving the Performance of the Cyberlink Mental Interface With the 'Yes/No Program'", Proceedings of CHI 2001 Mar. 31-Apr. 5, 2001 Settle, WA, USA; [CHI Conference Proceedings, Human Factors in Computing Systems], CHI 2001 Conference Proceedings, Conference on Human Factors in Computing Systems ACM New York, NY, USA, Mar. 31, 2001, pp. 69-76.
(Continued)

*Primary Examiner* — William Lu
(74) *Attorney, Agent, or Firm* — DLA Piper LLP US

(57) ABSTRACT

A system and method for controlling a non-tactile device including a receiving device configured to receive signals corresponding to a user's brain waves or movements, the brain waves or movements corresponding to a series of directional intentions, the intentions defining at least one line pattern, a processor configured to process the at least one line pattern, each of said at least one line patterns associated with an action of the device, and output a control signal to the non-tactile device related to the action.

20 Claims, 8 Drawing Sheets

Related U.S. Application Data continuation of application No. 16/142,279, filed on Sep. 26, 2018, now Pat. No. 10,809,803, which is a continuation of application No. 15/186,910, filed on Jun. 20, 2016, now Pat. No. 10,126,816, which is a continuation of application No. 14/295,733, filed on Jun. 4, 2014, now Pat. No. 9,405,366.

(60) Provisional application No. 61/886,045, filed on Oct. 2, 2013.

(51) Int. Cl.
- A61B 5/245 (2021.01)
- A61B 5/316 (2021.01)
- A61B 5/369 (2021.01)
- G06F 16/435 (2019.01)
- G06F 16/635 (2019.01)

(52) U.S. Cl.
CPC ............ A61B 5/369 (2021.01); G06F 16/436 (2019.01); G06F 16/636 (2019.01); *A61B 2562/0219* (2013.01); *A61B 2562/028* (2013.01); *G06F 2203/011* (2013.01)

(58) Field of Classification Search
CPC ......... A61B 5/245; A61B 5/316; A61B 5/369; A61B 2562/0219; A61B 2562/028
See application file for complete search history.

(56) References Cited

U.S. PATENT DOCUMENTS

| | | | |
|---|---|---|---|
| 5,474,082 A | 12/1995 | Junker | |
| 5,638,826 A * | 6/1997 | Wolpaw | G06F 3/015 345/157 |
| 5,724,987 A * | 3/1998 | Gevins | A61B 5/7264 434/258 |
| 5,840,040 A | 11/1998 | Altschuler et al. | |
| 6,024,700 A | 2/2000 | Nemirovski et al. | |
| 6,349,231 B1 * | 2/2002 | Musha | A61B 5/378 600/300 |
| 6,353,754 B1 | 3/2002 | Fischell et al. | |
| 6,377,833 B1 | 4/2002 | Albert | |
| 6,402,520 B1 * | 6/2002 | Freer | G09B 19/00 434/362 |
| 6,503,197 B1 | 1/2003 | Nemirovski | |
| 6,529,773 B1 * | 3/2003 | Dewan | A61B 5/375 600/544 |
| 6,636,763 B1 * | 10/2003 | Junker | G06F 3/013 345/157 |
| 6,829,502 B2 | 12/2004 | Hong et al. | |
| 6,952,809 B2 * | 10/2005 | Beranek | G06F 3/015 345/157 |
| 6,983,184 B2 * | 1/2006 | Price | A61B 5/377 607/45 |
| 7,120,486 B2 * | 10/2006 | Leuthardt | G06F 3/015 600/545 |
| 7,209,788 B2 * | 4/2007 | Nicolelis | G06F 3/016 600/545 |
| 7,260,430 B2 | 8/2007 | Wu et al. | |
| 7,580,742 B2 | 8/2009 | Tan et al. | |
| 7,706,871 B2 | 4/2010 | Devlin et al. | |
| 8,157,609 B2 * | 4/2012 | Hallaian | A63F 9/0079 446/173 |
| 8,692,769 B1 * | 4/2014 | Bendickson | G06F 3/01 345/157 |
| 8,786,546 B1 * | 7/2014 | Bendickson | G06F 3/015 345/8 |
| 8,823,674 B2 | 9/2014 | Birnbaum et al. | |
| 9,042,201 B2 | 5/2015 | Tyler et al. | |
| 9,092,055 B2 * | 7/2015 | Chen | G06F 3/01 |
| 9,114,940 B2 * | 8/2015 | Kraegeloh | A63F 3/00 |
| 9,405,366 B2 * | 8/2016 | Segal | G06F 16/436 |
| 9,420,960 B2 * | 8/2016 | Lazarewicz | A61B 5/369 |
| 9,740,285 B2 | 8/2017 | Beaty | |
| 9,900,498 B2 * | 2/2018 | Kim | H04N 1/00564 |
| 9,910,298 B1 * | 3/2018 | Sales | G02C 11/10 |
| 10,149,958 B1 * | 12/2018 | Tran | G16H 50/20 |
| 2002/0103429 A1 | 8/2002 | Decharms | |
| 2003/0046254 A1 * | 3/2003 | Ryu | G06F 3/015 706/15 |
| 2004/0117098 A1 | 6/2004 | Ryu et al. | |
| 2005/0131311 A1 * | 6/2005 | Leuthardt | A61B 5/24 600/545 |
| 2005/0153268 A1 | 7/2005 | Junkin et al. | |
| 2005/0177058 A1 | 8/2005 | Sobell | |
| 2006/0125659 A1 * | 6/2006 | Kim | G06F 3/015 341/20 |
| 2006/0192078 A1 * | 8/2006 | Yang | G06F 3/017 250/208.1 |
| 2007/0118400 A1 * | 5/2007 | Morita | G16H 40/20 705/2 |
| 2007/0123350 A1 * | 5/2007 | Soderlund | A63F 13/10 273/460 |
| 2007/0220108 A1 * | 9/2007 | Whitaker | H04M 1/6041 709/217 |
| 2008/0059578 A1 * | 3/2008 | Albertson | G06F 3/016 352/85 |
| 2008/0208072 A1 * | 8/2008 | Fadem | A61B 5/291 600/544 |
| 2009/0099474 A1 * | 4/2009 | Pineda | A61B 5/386 600/545 |
| 2009/0221928 A1 | 9/2009 | Einav et al. | |
| 2009/0306531 A1 | 12/2009 | Leuthardt et al. | |
| 2009/0318826 A1 * | 12/2009 | Green | A61B 5/7246 600/545 |
| 2010/0016732 A1 * | 1/2010 | Wells | A61N 1/36003 600/476 |
| 2010/0040292 A1 | 2/2010 | Clarkson | |
| 2010/0100001 A1 | 4/2010 | Aguilar et al. | |
| 2011/0074668 A1 * | 3/2011 | Mandanapu | G06F 3/038 345/156 |
| 2012/0049998 A1 | 3/2012 | Lim et al. | |
| 2012/0090003 A1 * | 4/2012 | Dove | H04N 21/42201 725/38 |
| 2012/0220889 A1 | 8/2012 | Sullivan et al. | |
| 2013/0051614 A1 * | 2/2013 | Lee | G06V 40/28 382/103 |
| 2013/0096453 A1 | 4/2013 | Chung et al. | |
| 2013/0106707 A1 | 5/2013 | Chen | |
| 2013/0106742 A1 | 5/2013 | Lee et al. | |
| 2013/0179087 A1 | 7/2013 | Garripoli | |
| 2013/0211238 A1 | 8/2013 | Decharms | |
| 2013/0242262 A1 * | 9/2013 | Lewis | H04L 5/0073 351/209 |
| 2013/0315425 A1 * | 11/2013 | Lunner | H04R 25/00 381/323 |
| 2013/0346168 A1 | 12/2013 | Zhou et al. | |
| 2014/0058528 A1 * | 2/2014 | Contreras-Vidal | A61B 5/291 600/383 |
| 2014/0078049 A1 * | 3/2014 | Parshionikar | G06V 20/20 345/156 |
| 2014/0267024 A1 * | 9/2014 | Keller | G06F 3/014 345/156 |
| 2014/0277582 A1 * | 9/2014 | Leuthardt | A61B 5/0006 623/25 |
| 2015/0045007 A1 * | 2/2015 | Cash | A61B 5/374 455/418 |
| 2015/0313496 A1 * | 11/2015 | Connor | A61B 5/369 600/301 |
| 2016/0103487 A1 * | 4/2016 | Crawford | A61B 5/117 600/544 |
| 2016/0109961 A1 * | 4/2016 | Parshionikar | G06F 3/013 345/156 |
| 2016/0235323 A1 * | 8/2016 | Tadi | A61B 5/0006 |

(56) References Cited

U.S. PATENT DOCUMENTS

2017/0003750 A1* 1/2017 Li .......................... G06F 3/017
2017/0249009 A1* 8/2017 Parshionikar ........... G06F 3/017

OTHER PUBLICATIONS

European Search Report for Application No. 18210066.9-1216 dated Mar. 11, 2019.
Machine Translates Thoughts into Speech in Real Time, http://phys.org/print180620740.html, Dec. 21, 2009.
Wolpaw et al, "Brain-computer interfaces for communication and control", Clin Neurophysiol, Elsevier, vol. 113, pp. 767-791, Dec. 2002.
Wolpaw et al, "Control of a two-dimensional movement signal by a noninvasive brain-computer interface in humans", PNAS, vol. 101, No. 51, pp. 17849-17854, Dec. 21, 2004.

* cited by examiner

SYSTEMS AND METHODS FOR USING IMAGINED DIRECTIONS TO DEFINE AN ACTION, FUNCTION OR EXECUTION FOR NON-TACTILE DEVICES

CROSS-REFERENCE TO RELATED APPLICATIONS

This application is a continuation of U.S. application Ser. No. 17/073,717, filed Oct. 19, 2020, which is a continuation of prior U.S. application Ser. No. 16/142,279, filed on Sep. 26, 2018, now U.S. Pat. No. 10,809,803, issued Oct. 20, 2020, entitled "SYSTEMS AND METHODS FOR USING IMAGINED DIRECTIONS TO DEFINE AN ACTION, FUNCTION OR EXECUTION FOR NON-TACTILE DEVICES", which is a continuation of U.S. application Ser. No. 15/186,910, filed on Jun. 20, 2016, now U.S. Pat. No. 10,216,816, issued Nov. 13, 2018, entitled "SYSTEMS AND METHODS FOR USING IMAGINED DIRECTIONS TO DEFINE AN ACTION, FUNCTION OR EXECUTION FOR NON-TACTILE DEVICES", which is a continuation of prior U.S. application Ser. No. 14/295,733, filed on Jun. 4, 2014, now U.S. Pat. No. 9,405,366, issued Aug. 2, 2016, entitled "SYSTEMS AND METHODS FOR USING IMAGINED DIRECTIONS TO DEFINE AN ACTION, FUNCTION OR EXECUTION FOR NON-TACTILE DEVICES", which in turn claims the benefit of U.S. Provisional Application No. 61/886,045, filed Oct. 2, 2013, each of which being incorporated by reference in its entirety.

FIELD OF THE INVENTION

The present invention relates to the control and operation of non-tactile devices and, more particularly, to a system and method for using imagined directions, such as up, down, left and right, that together define a single action, function or execution for non-tactile devices.

BACKGROUND OF THE INVENTION

There is an emerging market in the information technology sector that focuses on the reading of brain waves in order to operate devices or to generate speech communication. Devices that read brain waves and control devices are commonly referred to as brain-computer interfaces (BCI), mind-machine interfaces (MIMI), direct neural interfaces (DNI), synthetic telepathy interfaces (STI) or a brain-machine interfaces (BMI).

A BCI is a system in which messages or commands that a user sends to the external world do not pass through the brain's normal output pathways of peripheral nerves and muscles. For example, in an electroencephalography (EEG)-based BCI, the messages are encoded in EEG activity. A BCI provides its user with an alternative method for acting on the world. For more information on BCIs, see Wolpaw, Jonathan R., N. Birbaumer, D. J. McFarland, G. Pfurtscheller, and T. M. Vaughan, "Brain-computer interfaces for communication and control," *Clinical Neurophysiology*, 113 (2002) 767-791, which is hereby incorporated by reference in its entirety.

A BCI changes electrophysiological signals from mere reflections of central nervous system (CNS) activity into the intended products of that activity: messages and commands that act on the world. It changes a signal such as an EEG rhythm or a neuronal firing rate from a reflection of brain function into the end product of that function: an output that, like output in conventional neuromuscular channels, accomplishes the user's intent. Id. As such, a BCI replaces nerves and muscles and the movements they produce with electrophysiological signals and the hardware and software that translate those signals into actions. Id. A BCI operation depends on the interaction of two adaptive controllers: the user's brain, which produces the signals measured by the BCI; and the BCI itself, which translates these signals into specific commands. Id.

Currently, devices such as EEG headsets have become readily available to the retail market. These devices read the brain's six wave types, or "bands", and classifies them into one of the following categories:

TABLE 1

The six (6) wave types emitted by a typical brain during normal thought processes, including their frequency ranges and normal correlative behavior.

| BAND | FREQUENCY (Hz) | NORMAL |
| --- | --- | --- |
| Delta | Up to 4 | Adult slow-wave sleep; In babies; Present during "continuous" tasks; |
| Theta | 4-7 | Drowsiness; Arousal in adults; Idling |
| Alpha | 8-12 | Relaxation/Reflection; Closing the eys; Inhibition control |
| Beta | 13-30 | Alertness; Active or anxious thinking |
| Gamma | 30-100+ | Multiple perceptions, such as "sight and sound"; Short-term memory matching of recognized objects; |
| Mu | 8-13 | Rest-state motor neurons |

EEG devices read the bands of brain activity which present themselves as electrical waves. Typically, these waves are read in real-time, interpreted and then associated to a pre-defined action resulting in a "one-to-one correlation", meaning the user thinks "X" and the device either speaks "X" or executes "X".

Devices exist that can convert a user's thought to a direction (e.g. a direction along the axis) or movement (e.g., movement of a body part of a user, or movement of an external object), in that a user imagines a movement or direction, such as "left", or "ball moves up", or "hand moves down", which creates an easily identifiable wave pattern for the EEG to read, and the EEG sends this pattern to proprietary software which can then send a suitable corresponding (e.g. "left") command to something as simple as a computer cursor or mouse pointer to something physical, such as a wheelchair, car or other device, or can use the thought as a component into an output of item of information.

Examples include that a user thinks "left" which results in something moving left (e.g., a prosthetic appendage, a mouse pointer, etc.).

There are inherent challenges in the existing modality of one-to-one correlations with regards to the association of brain wave patterns in spoken language or executed actions. The only way researchers have been successful with accurate and fast thought-to-speech technologies has been to implant computer chips within the brains of the users, often involving open-brain surgery. The existing thought-to-speech technologies often attempt to identify common/frequent "patterns" within the brain waves of spoken and "non-spoken/thought/imagined" language. Many times, these patterns can be the same for words that are similar: cat, rat, bat, mat, etc. Or, similar phrases such as, "I hate cats" and "irate bats". Even with implanted chips, users can expect a success rate of between 45% and 89%. For more on thought-to-speech, see "Machine Translates Thoughts into Speech in Real Time", Dec. 21, 2009, "phys.org", which is hereby incorporated by reference in its entirety.

If an "over-the-counter" EEG machine is incorporated with the existing modalities of brain wave interpretation, the resolution of the device is typically not accurate enough to identify the intended thought consistently to be useful in day-to-day practice. Not only is the general interpretation of brain waves and specific brain wave patterns very difficult due to their dynamic nature and high variability, but outside electrical interference from commonly used devices, such as cell phones and televisions, make this process even more difficult and the output more inaccurate.

The challenges in the user's thought-to-command category of thought-controlled devices are nearly identical with the above thought-to-speech category. Problems with correctly identifying the non-verbalized command greatly affect the selection of the associated action.

There are also challenges with the user's thought-to-direction category. These one-to-one correlations of non-spoken commands/thoughts into the direction of "something" is by far the most accurate and repeatable process for all thought-controlled devices. Up, down, left and right are all consistent, repeatable patterns, and might be the most easily identifiable markers within commonly collected EEG brain wave data. However, this category is limited in that researchers and inventors are only using this logic to associate directional-based thoughts with the movement of an object (e.g., movement of a mouse pointer, movement of a computer cursor, operation of a wheelchair, driving a car, operating an exoskeleton, or the like), which remains a one-to-one correlation of "imagined direction" with the actual executed direction, whether it be virtual via software or mechanical via devices and equipment.

This challenge/limitation leaves a huge void in controlling devices that are not operated with directional thought. For example, controlling, using thought, devices such as televisions, doors, appliances, adjustable beds or even mobile phones and tablet computers is not easily done using conventional methods. The answer would lead one to operate within the thought-to-speech or thought-to-command modalities, which are highly unreliable and unpredictable. It would not necessarily lead one to operate within the thought-to-direction modality due to the traditionally perceived limitation of a finite number of directional thoughts.

As can be seen, there is a need for improved methods for using thoughts and other input to define a single action, function or execution for non-tactile (e.g., not requiring touch input as is required with a keyboard or mouse) or thought-controlled devices that is more reliable and accurate.

SUMMARY

One embodiment includes the use of patterns or line patterns and directional or movement intentions, or templates, which correspond to a user's (humans, typically) thought (e.g., imagined directions or movements), for the execution of actions, including, without limitation, thought-to-speech by associating patterns to pre-defined words, phrases or number, thought-to-control by associating patterns to pre-defined actions or a series of actions, and thought-to-direction by associating patterns to directions or "direction concepts" that cannot be defined with a simple up, down, left, or right thought or intention, which include, without limitation, diagonals, turns of different degrees, forwards/backwards in 3-dimensional environments, and/or complicated sets of "directions" outside the gamut of "up, down, left, or right".

Accordingly, an embodiment the present invention provides a system for controlling a device or transmitting information including a movement or direction intention receiver or brain-scanning device configured to receive signals corresponding to a user's brain waves or movements, said brain waves or movements corresponding to a series of directional intentions, the intentions defining at least one line pattern, a processor configured to process, convert or translate the at least one line pattern, each of said at least one line patterns associated with an action of the device. A control signal (e.g., an electrical signal, an infrared signal, etc.) may be output to the device requesting that the device perform the action. A device controller may be configured to perform the action.

An embodiment of the present invention provides a method for controlling a receiver or device including obtaining or receiving signals corresponding to brain waves or movements, the brain waves or movements corresponding to a series of directional intentions defining a line pattern associated with an action of the device. A control signal (e.g., an electrical signal, an infrared signal, etc.) may be output to the device requesting that the device perform the action. A device controller may be configured to perform the action.

A further embodiment of the present invention provides a method for interpreting brain waves or movements, each brain wave or movement corresponding to a direction, converting the brain waves or movements (or signals corresponding to brain waves or movements) into a series of directions, and converting the series of directions into an item of information. In certain embodiments, the item of information includes a command to a device, a set of commands to a device, a character, a numeral a word, a sentence or an entire paragraph. In certain embodiments, the series of directions is defined as a unit including at least one part, each part having at least one brain wave or movement converted to a corresponding direction. In some embodiments, the set of brain waves or movements include brain waves or movements corresponding to at least two dimensions of direction. In some embodiments, converting the series of directions to the item of information includes searching a database for a corresponding series of directions, the corresponding series of directions being associated with the item of information, and matching the series of directions with the corresponding series of directions.

BRIEF DESCRIPTION OF THE DRAWINGS

The principles and operation of the system and method according to the present invention may be better understood with reference to the drawings, and the following description, it being understood that these drawings are given for illustrative purposes only and are not meant to be limiting, wherein.

Figure 1:
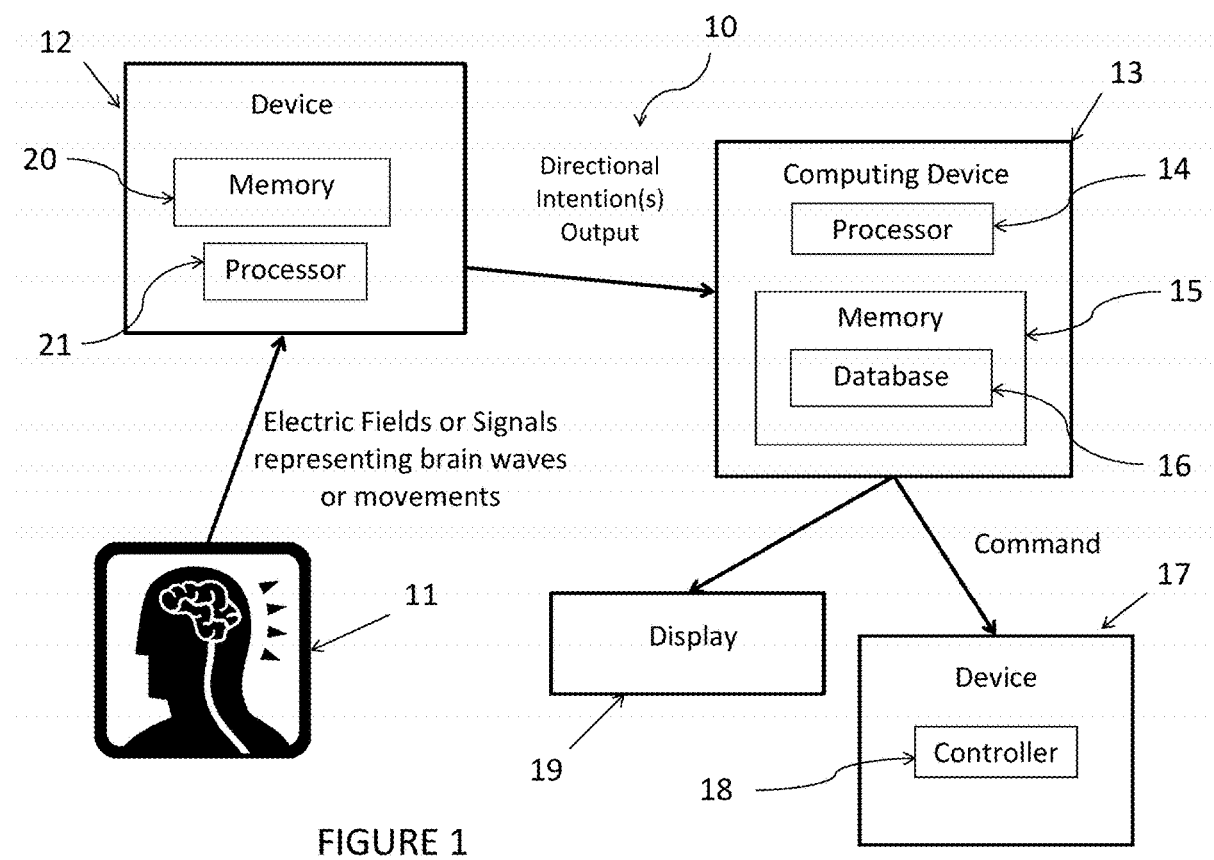
FIG. 1 is an illustration a system according to certain embodiments of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of the invention. However, it will be understood by those of ordinary skill in the art that the present invention may be practiced without these specific details. In other instances, well-known methods, procedures, components and circuits have not been described in detail so as not to obscure the present invention.

Unless specifically stated otherwise, as apparent from the following discussions, it is appreciated that throughout the specification discussions utilizing terms such as "processing", "computing", "storing", "determining", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. Such apparatuses may be specially constructed for the desired purposes, or may comprise controllers, computers or processors selectively activated or reconfigured by a computer program stored in the computers. Such computer programs may be stored in a computer readable storage medium (e.g., a non-transitory computer readable storage medium), such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus. It will be appreciated that a variety of programming languages may be used to implement the teachings of the invention as described herein.

Embodiments of the invention may include electronic circuitry, wired or wireless transmitters and receivers, input-output ("I/O") interfaces/devices, and one or more controllers. A receiver may be used, for example, to receive control information (e.g., to change a mode of operation, to change the value of a parameter, etc.) and various messages.

Embodiments of the invention may include various devices that utilize one or more wireless communication technologies such as, without limitation, radio frequency (RF), free-space optical, ultrasonic and electromagnetic induction. Embodiments of the present invention my include wireless communication devices such as, without limitation, RF devices, infrared and ultrasonic remote control devices, cellular devices, global positioning system (GPS) devices, wireless USB devices, and BLUETOOTH® devices. For example, communication from a movement or directional intention receiver or brain-scanning device to a computing device, or a command transmitted from a computing device, may be wireless. For example, certain embodiments of the present invention may utilize micro gyroscopes, accelerometers and/or MEMS devices that detect minute movements corresponding to a directional intention, and wirelessly transmit output corresponding to the directional intention via RF or BLUETOOTH® devices. Such movements may be not obvious, or difficult or impossible to detect with the unaided eye, such as jaw clenches, blinking, etc. Such movements may be read by a receiver and converted to directional intentions as with brain waves or brain signals (e.g., the waves discussed in Table 1, above, or other detectable brain waves or brain signals), as discussed herein.

Embodiments of the invention may include an article such as a computer or processor readable medium, or a computer or processor storage medium, such as for example a memory, a disk drive, or a USB flash memory, encoding, including or storing instructions, e.g., computer-executable instructions that, when executed by a processor or controller, carry out methods disclosed herein. Processors may include any standard data processor, such as a microprocessor, multiprocessor, accelerator board, or any other serial or parallel high performance data processor.

Embodiments of the invention may be included as part of a computing system, such as, for example, a personal computer or workstation which includes standard components such as an operating system, a processor, a memory, a disk drive, and input-output devices. Embodiments of the present invention may be compatible or integrated with any operating system on any device including, without limitation, the OSX operating system or WINDOWS® operating system. Alternative computer configurations are possible, and the system and method of the present invention may be implemented on various suitable computing systems, including, without limitation, hand-held, mountable or mobile computing systems. In certain embodiments, mobile computing systems may include, without limitation, mobile smartphones running iOS, WINDOWS®, ANDROID® OR LINUX® operating systems.

In certain embodiments, the system of the present invention may be wearable such as, for example, mounted on a garment of a user. For example, the movement or directional intention receiver or brain-scanning devices discussed below may be wearable. However, other options for hands-free (non-tactile) systems exist.

As generally known in the art, directional thoughts are the most recognizable intentions within a user's brain waves. In the article "Brain-computer interfaces for communication and control" cited above (and incorporated herein), J. R. Wolpaw identifies the directional thoughts as mu and beta rhythms. Specifically, in users that are awake, primary sensory or motor cortical areas often display 8-12 Hz EEG activity when they are not engaged in processing sensory input or producing motor output, which is generally referred to as mu rhythm. Mu rhythm activity comprises a variety of different 8-12 Hz rhythms, distinguished from each other by location, frequency, and/or relationship to concurrent sensory input or motor output. These mu rhythms are usually associated with 18-26 Hz beta rhythms. While some beta rhythms are harmonics of mu rhythms, some are separable from them by topography and/or timing, and thus are independent EEG features. See Wolpaw et al., "Brain-computer interfaces for communication and control", at pg. 775.

Several factors suggest that mu and/or beta rhythms could be good signal features for EEG-based communication. They are associated with those cortical areas most directly connected to the brain's normal motor output channels. Movement or preparation for movement is typically accompanied by a decrease in mu and beta rhythms, particularly contralateral to the movement. This decrease has been labeled "event-related desynchronization" or ERD. The opposite, rhythm increase, or "event-related synchronization" (ERS) occurs after movement and with relaxation. Importantly, and most relevant to the present invention, ERD and ERS do not require actual movement and they can also occur with motor imagery (e.g., imagined movement). Id.

The above observations concerning mu/beta rhythms have been used in the art to control movement of a cursor in one or two dimensions to targets on a computer screen. Typically a user increases the amplitude of an 8-12 Hz mu rhythm to move a cursor to a target at the top of the screen or decreases it to move to a target at the bottom. Frequency spectra for top and bottom targets show that control is clearly focused in the mu-rhythm frequency band. Sample EEG traces also show that the mu rhythm is prominent with the top target and minimal with the bottom target. Id.

For each dimension of cursor control, a linear equation translates mu- or beta-rhythm amplitude from one or several scalp locations. Id. It has also been shown that a user can achieve independent control of two different mu- or beta-channels and thus use that control to move a cursor in two dimensions (e.g. up/down and left/right). Id., at pg. 776.

In particular, it has been shown that a noninvasive BCI, using sensorimotor rhythms recorded from the scalp of a human user, can provide multidimensional control. For more information on multidimensional control see Wolpaw, J. R. and D. J. McFarland, "Control of a two-dimensional movement signal by a noninvasive brain-computer interface in humans", Proceedings of the National Academy of Sciences, vol. 101(51), pgs. 17849-17854, Dec. 21, 2004, which hereby incorporated by reference in its entirety. In this study, EEG activity was recorded from 64 standard electrode locations distributed over the entire scalp. All 64 channels were referenced to the right ear, amplified 20,000× (bandpass 0.1-60 Hz), digitized at 160 Hz, and stored. A small subset of the 64 channels controlled cursor movement on a screen. Each dimension of cursor movement was controlled by a linear equation in which the independent variable was a weighted combination of the amplitudes in a mu (8-12 Hz) or beta (18-26 Hz) rhythm frequency band over the right and left sensorimotor cortices. The results of the study show that human users can learn to use scalp-recorded EEG rhythms to control rapid and accurate movement of a cursor in two dimensions.

Embodiments of the present invention generally feature a brain-computer interface (BCI), mind-machine interface (MMI), direct neural interface (DNI), synthetic telepathy interface (STI) brain-machine interface (BMI), or the like, including an input (e.g., electrophysiological activity from the user), output (e.g., device commands or information such as text, sentences, or words), components and/or processors that translate input into output, and other components such as a protocol that determines the onset, offset, and timing of operation (see J. R. Wolpaw et al., "Brain-computer interfaces for communication and control", cited above and incorporated herein by reference). Other or different functionality or components may be included.

Movement or directional intention receivers and brain-scanning devices are generally known in the art. Examples of known receivers and brain-scanning devices include, but are not limited to, electroencephalography (EEG) devices, including known EEG software applications, micro gyroscopes, accelerometers, microelectromechanical systems (MEMS), motion-detecting infrared sensors, magnetic resonance imaging (MM), nuclear magnetic resonance imaging (NMRI) or magnetic resonance tomography (MRT) or the like, and/or magnetoencephalography (MEG) devices. Specific examples of "over-the-counter" brain-scanning devices may include, without limitation, the EPOC brain-scanning device by the company Emotiv, and the MINDWAVE® brain-scanning device by the company NeuroSky. Typically such devices detect electric, magnetic or other signals produced by the brain which correspond to brain waves, thought or mental states. Other devices, such as micro gyroscopes, accelerometers and MEMS devices may detect minute movement such as movement of a user's hand or head which correspond to a directional intention. However, it is understood that the embodiments of the present invention are hardware agnostic.

Without limitation, embodiments of the present invention utilize movement or directional intention receivers and/or brain-scanning devices that are capable of detecting or receiving and identifying various signals, movements, thought and/or brain wave or brain signal patterns associated with particular thought actions such as, for example, directional or movement-related thoughts (e.g., up, down, left, right, etc.). A conversion or translation from movements or brain waves to directions may be performed, and a conversion or translation from directions to information (e.g., words, commands, etc.) may be performed. In preferred embodiments, the brain-scanning device is non-invasive, but may be in other embodiments.

In accordance with certain embodiments of the present invention, a brain-scanning device (e.g., an EEG) may be used to measure mu/beta rhythms of a user's brain to produce directional thoughts (e.g., up, down, left, right) as an output. In certain embodiments, the directional thoughts may be in one dimension as either vertical (e.g. up or down) or horizontal (e.g., left or right) thoughts. In other embodiments, the directional thoughts may be in two dimensions including both vertical and horizontal thoughts. More dimensions of directional thoughts are contemplated, such as, without limitation, diagonal dimensions. Other types of brain waves or signals may be used.

Directional thoughts, as used herein, may be interpreted to mean "thought-to-direction" directional intentions, directional cogitations, directional concepts, directional impressions or the like. In general, a directional intention is a thought generated by the brain of a user (e.g., a human) that corresponds to a known directional command such as, without limitation, up, down, right and left, but could also include such directional thoughts as, inter alia, diagonal, sideways, front, back, north, south, east, and west. Other general intentions, other than directions, which may be embodied as thoughts by a user, may be used. Embodiments of the present invention utilize directional intentions that are easily identifiable, accurate and distinguishable from one another, such as, without limitation, directional intentions resulting in identifiable patterns in mu/beta rhythm frequencies, or directional intentions resulting from a user's movement (e.g., hand wave, jaw clench, or head tilt).

In certain embodiments of the present invention, a directional intention may be understood as representing a single direction. For example, a first directional intention may represent "down", a second directional intention may represent "left", and a third directional intention may represent "up", etc. As used herein, a series or plurality of directional intentions may represent a series of individual directional intentions such as, for example only, "up" and "right" and "down" and "left".

A collection, set or series (e.g., an ordered series or ordered set) of two or more directional intentions may be referred to herein, and represented visually, as a pattern or a line pattern. By combining directional intentions into a single line pattern, the result is the "lowest common denominator" in a super-efficient, super-accurate and nearly infinite command base that originates from a user's imagined thought to any electrical device—computers, laptops, mobile devices, wearable computers, implanted processors, nano-computers, or the like. Embodiments of the present invention may replace computing input devices such as keyboards. By collecting directional intentions into a single "line template", a user can have an infinite platform from which to define any and all computing actions in a near 100% repeatable fashion. This would also include thought-to-speech modalities by defining words, sentences and may be entire paragraphs to a line template. Embodiments may be used for functions other than device control, such as producing or transmitting messages, words, sentences, etc. While patterns connected by lines are shown, other patterns corresponding to detected or received thoughts, movements or brain signals may be used.

While examples used herein focus on line patterns, shapes or runes being created based on brain waves or brain signals, note that in some embodiments line patterns, shapes, and runes may be arbitrary representations of brain waves, and embodiments may take thoughts, assign thoughts to building blocks (e.g., directions, bits, segments) of information, and translate sequences of these building blocks to information (e.g., characters, letters, commands, etc.).

The phrase line pattern, as used herein, may be interpreted to mean a symbol, letter, numeral, character, glyph, icon, sign, line template or the like. Line patterns may be commonly referred to herein as a "rune" with respect to a graphical representation of the line pattern. In the example used above, the line pattern (e.g., rune) for the series of directional intentions "up, right, down, left" may appear graphically as a rectangle or square. In certain embodiments, directional intentions or other recognized intentions may have a depth. As used in this context, depth may mean the length or duration of a thought such as, for example, thinking "up" persistently for more than one second or for multiple seconds. In certain embodiments, depth may allow for differentiation between symbols or signals such as, for example, a rectangular rune and a square rune, each having its own distinct definition or associated action. In alternative embodiments, the series of directional intentions may not be graphically represented as a line pattern as bracketed directional intentions, e.g. [up, right, down] or [U,R,D].

Embodiments of the present invention may be operated by one or more individual directional intentions, by one or more line patterns that include two or more directional intentions, or by a combination of both.

In broad terms, certain embodiments of the present invention include line patterns that define, without limitation, any action, procedure or execution. In this way, a first combination of two or more directional intentions (e.g., a first line pattern) may define a first action, procedure or execution, while a second combination of two or more directional intentions (e.g., a second line pattern) may define a second action, procedure or execution.

It is understood that the line patterns, or line templates, of embodiments of the present invention may take any form from the most simple to the most complex and include any number of different combinations and possibilities, resulting in any number of distinct line patterns. Each line pattern may be as simple as two directional intentions and may be as complicated as desired, including without limitation, three (3), five (5), ten (10), fifty (50), or one hundred (100) or more directional intentions.

Line patterns may represent the "written language" for all thought-controlled devices and thought-to-speech applications that cannot operate on a one-to-one correlation. In this way, line patterns may represent a "cognitive language" having symbols, runes or glyphs representative of a particular meaning or defining a particular action. That is, it is contemplated in embodiments of the present invention that the directional intention "up" does not necessary correlate to an upwards movement, but may be assigned another action such as turning a device on. In the same manner, a series of two or more directional intentions (e.g., a line pattern) may be assigned to any operation, action, procedure or execution. As used herein, a line pattern can be assigned to any action or collection of actions, which makes is possible to create a near limitless library of "thought-to-something" commands/actions, resulting in a "mind operating system to everything".

Line patterns may be defined by an end-user, a manufacturer, or both. In certain embodiments, a single line pattern may be associated with a single executable action or may be associated with a collection of executable actions. In certain embodiments, line patterns may be assigned to a collection of other line patterns, sometimes referred to herein as a "plaque", that may serve as a directory, folder and/or menu. A line pattern may be associated with a character, numeral, symbol, word, sentence, paragraph, meta-character or punctuation mark (e.g., period, carriage return, end-of-word, etc.).

As used herein, a plaque may be understood to mean a collection of line patterns affiliated with a certain category of related subject matter. For example, a plaque may represent a folder structure, icon or location on a computing device as known in the art. In another example, a plaque may represent a directory, such as a phone number and/or address directory. In certain embodiments of the present invention, a particular line pattern may be assigned to the plaque to operate as a command to open, use or browse the plaque. In other examples, a plaque may represent a series of related commands such as, for example, a plaque for turning on a home theatre system including, without limitation, commands to turn on a television, a media player and a speaker system. In this example, a single line pattern affiliated with the plaque may operate all of these commands.

In certain embodiments, entire operating systems may be written to operate and respond using a library of directional intentions, line patterns, and plaques. A mental operating system (MOS), for example, can be created to include line pattern templates and their definitions of actions and executions. With certain embodiments of the present invention entire software applications may be written without tactile input and visual output.

For example, certain embodiments of the present invention include a cognition operating system (COS). The COS may include, without limitation, four components. The first component may be a thought-to-action component using line patterns to launch one or more applications and to perform core functions (e.g., ALT, CTRL, DELETE, search, volume). A second component may be a thought-to-input component utilizing an alphabet plaque incorporating adaptive/predictive logic to predict the intended complete input from only a small amount of entered input, and which may include systems for storing common choices of predictive behavior as a particular line pattern. A third component may be a thought-to-speech component including user-defined line patterns for words, phrases or paragraphs, manufacturer-defined line patterns for words, phrases or paragraphs, and ad-hoc speech using four (4) line pattern inputs for noun, verb, adjective and emotion/tone. This latter component may include plaques encompassing distinct line patterns for, for example, the (e.g. 25) most common nouns, most common verbs, and most common pronouns used in a language. A fourth component may be a thought-to-control component, including output to third party devices, and may include manufactured devices having pre-defined line patterns for thought-controlled operation that report back to the COS via, for example, WIFI or BLUETOOTH® devices on COS-compatibility and import associated line patterns and line pattern definitions.

In addition, certain embodiments of the present invention may include a cognition user interface (CUI), including a library of defined line patterns or pulse sets organized into plaques. The basic structure of a CUI may include, for example, the four COS components discussed above organized as a user interface as known in the art. CUI input may include universal commands of basic directional intentions. For example, a short "up" burst directional intention may move a user's intended menu selection one menu higher, a short "down" burst directional intention may move a user's intended menu selection one menu lower, a long persistent "up" directional intention may bring a user back to the MAIN menu, a long persistent "down" directional intention may execute the current selection, a short "left" burst directional intention may move the intended menu selection one menu to the left, and a short "right" burst directional intention may move the intended menu selection one menu to the right. CUI output may include visual and audible output, including without limitation, text-to-speech or thought-to-speech.

The systems and methods of certain embodiments of the present invention may include a wearable movement or directional intention receiver or brain-scanning device, such as a micro gyroscope, an accelerometer, a MEMS, or an EEG or other similar device, or combination of devices, which can read a user's movements or brain waves or brain signals representing directional intentions, identify the directional intention as thoughts related to up, down, left and right, and provide these directional intentions as output (e.g., digital output). The output can be delivered to a computing device having a processor for receiving output from the EEG. The processor may translate or convert the directional intention(s) into a line pattern, identify an action (or other operation) or word, character sentence or other information associated with the line pattern, and, for example, produce output, or send a command or control signal to a controller to perform that action, function or execution. The line pattern may be converted or translated to information (e.g., words, commands, etc.).

In certain embodiments of the present invention, users may control wearable computers, or devices, that might be too small to have a computer screen/interface, and implanted computers and processors may be fully controlled by imagined (e.g., cogitated) line patterns.

Embodiments of the present invention can accept the output of any EEG device or movement receiver making the present invention hardware agnostic. In certain embodiments, a user may need training on an EEG device or other device discussed herein to operate it effectively. Input entering a computing device may be accepted as a valid directional intention (e.g., up, down, left, right) and the directional pattern (e.g. rune or line pattern) can be captured and stored to compare it to a database of runes.

Stored data may be compared to line patterns that exist within the current plaque, which is a collection of closely related line patterns. As brain waves or movements related to directional intentions are read by the brain-scanning device, the system according to certain embodiments may disqualify impossible line patterns in real-time to speed-up the processing of the final intended line pattern (e.g., adaptive/predictive logic). In this embodiment, if the line pattern begins with a certain intention, other intentions may be logically excluded. E.g., if the directional intention "down" is detected or received, the system may exclude as impossible all line patterns that begin with the directional intentions "up", "left" and "right". Once the intended line pattern is determined, the action assigned to that line pattern can be executed or the symbol, character, etc., may be recorded or output.

Embodiments of the present invention can read EEG or other brain signal or movement output, translate or convert the movement or brain waves (or signals corresponding to brain waves) to directional or movement intentions, collect multiple directional or other intentions in the correct order (based on pre-defined line pattern templates) and then execute an associated command or set of commands/actions, or output the corresponding information. Steps of a method according to certain embodiments of the present invention may include, in no particular order, defining the collection of directional intentions, in the correct order, that make up a line pattern, associating an action to the line pattern should a line pattern match occur, accepting input from any EEG, movement receiver or other brain-scanning device and identifying that input as a directional intention (e.g., up, down, left, right), comparing the accepted directional intentions to the definitions of pre-defined line patterns, and executing the pre-defined action associated to that line pattern should a line pattern match occur.

The methods, according to certain embodiments of the invention, provide simple processes that may occur in any order, be written in any computer language and executed in any number of ways. Various line patterns may be defined, and the use of these line patterns may be implemented within virtually any software application. Instructions for carrying out the various method steps according to certain embodiments of the invention may be written in any computer language using any modality of coding logic as known in the art.

In certain embodiments of the present invention, directional or other recognized intentions may have a depth. As used in this context, depth may mean the length or duration of a thought. For example, depth may include the user thinking "up" persistently for more than one second, or multiple seconds. In this context, and according to certain embodiments of the present invention, the directional intention may correlate to a first condition or action if imagined for one second, and may correlate to a second condition or action if imaged for more than one second (e.g., two or three seconds). The line pattern involving a "deeper" directional intention can have a different meaning than a line pattern not involving the "deeper" directional intention. The depth of a directional intention may be a component of any line pattern and references to lines patterns made herein may or may not include depth. That is, it is understood that embodiments of the present invention do not necessarily include or exclude depth of a directional intention.

A secondary solution for the weaknesses of conventional one-to-one correlative thought control is the use of pulsed concentration in a series of short and long pulses (similar to Morse Code, but user/manufacturer defined) for the execution of nearly anything, including, without limitation: (1) thought-to-speech, where a series of pulses is associated to pre-defined words, phrases or numbers; (2) thought-to-control, where a series of pulses are associated to pre-defined actions or series of actions.

In order to convey this secondary solution, a pulse set can be defined as a collection of two or more pulses of concentration (short and/or long), that are combined in order to execute a single pre-defined action (or set of actions) or to speak a word, sentence or pre-defined paragraph. The length of time for a short and long pulse can be user-defined or manufacturer-defined. Pulses of concentration may include jaw clenches or eye blinks.

In certain embodiments, a pulse set may be associated with pre-defined words, phrases or numbers. In another or the same embodiment, a pulse set may be associated with pre-defined actions or a series of actions.

Various uses of the embodiments of the present invention are contemplated. For example, complex control systems (e.g., cockpits or control panels) may be controlled with thought and without being physically in front of the controls.

Line patterns could be used in the medical sector during surgeries, and surgeons may handle their own drug administrations without the aid of assistants while never taking their hand off a scalpel. Severely handicapped people (e.g., individuals with neurological diseases and quadriplegics) may operate phones, televisions, appliances and nearly anything by using their thought and imagined directional thoughts and line patterns. Certain methods of some embodiments of the present invention may allow two or more people to have a conversation including pre-defined words, sentences or paragraphs by imaging the directional intentions and producing particular line patterns according to certain aspects of the present invention. This is critical in helping non-speaking individuals to communicate in real-time faster than they ever have before. Embodiments may help deaf individuals communicate with non-deaf individuals who do not know sign language.

Soldiers could communicate complete instructions to each other without being limited by hand-signals during close combat scenarios. Spies can have a face-to-face conversation with an intelligence asset while having a separate two-way secret conversation.

Business persons may have real-time conversations with each other while sitting in front of a client or prospect.

Additionally, embodiments of the present invention may be used as a universal thought-controlled interface for wearable or implanted computers and processors. Examples of such computers include Apple's iWatch™ wearable computer system or Google's Glass™ wearable computer system, and computers or devices that are so small and integrated that they do not have an input device or display. Any implanted chip or computer could easily use the line pattern/pulse set/plaque interface.

Reference is now made to FIG. 1, which is an illustration of a system 10 according to certain embodiments of the present invention. In system 10, a user 11 (e.g., a human) may think, or affect movement corresponding to, a series of directional thoughts or directional intentions. For example, user 11 may think to himself/herself a series of directional thoughts including down, down, down, which produces a series of identifiable, movements or electrical fields or signals representing brain waves or brain signals in user 11 that are detectable by movement or directional intention receiver or brain-scanning device 12. Device 12 may detect brain waves and translate or convert the brain waves (or signals corresponding to brain waves) to directional or movement intentions, identifies the series of directional intentions (in this example as down, down, down) and outputs the series of directional intentions to computing device 13 having computer controller or processor 14, memory 15 and database 16, and display 19. In some embodiments, the output from device 12 may be communicated wirelessly. Memory 15 may store database 16 and may also store other data such as, for example, software or code that may be executed by processor 14. Database 16 includes a collection of line patterns that are associated with a specific action, function, execution or the like. Processor 14 analyzes the series of directional intentions as a line pattern and searches database 16 for the specific line pattern (in this example as down, down, down). Once the line pattern is identified, processor 14 may send a command to device controller 18 of device 17 to perform the action, function or execution, or may record or output information corresponding to the line pattern, such as a character, numeral, word, or other item of information. In certain embodiments of the present invention, the identified line patterns may represent words, phrases or sentences that may for example be displayed on display 19 or output in another way or stored. Computer controller or processor 14 may be configured to carry out embodiments of the invention by, for example, executing software or code for example stored in memory 15. Thought patterns other than directional intentions may be used. While in one embodiment device 13 translates intentions to information, and device 12 translates brain waves to intentions, in other embodiments other or different units may perform these functions, and the functionality of devices 12 and 13 may be combined.

In certain embodiments, system 10 may include a combination of movement receiving devices and brain-scanning devices, and system 10 may receive input from one or from a combination of these devices. As such, directional intentions may correspond to signals received from movement or from brain waves.

As discussed above, movement or directional intention receiver or brain-scanning device 12 may be or include an EEG device, including known EEG software applications, a micro gyroscope, accelerometer, MEMS, a motion-detecting infrared sensor or reflector, a MRI device, a NMRI device, a MRT device or the like, and/or a MEG device, or combinations thereof. In preferred embodiments, device 12 allows non-tactile input to a computer. In general, the word "tactile"

is defined as: of or connected with the sense of touch. Therefore, non-tactile computing, such as, for example, the computing performed or enabled by device 12, relates to technologies and modalities that allow one to input data into a computer without having to touch it. A popular form of non-tactile input currently known in the art is voice recognition. In preferred embodiments, movement or directional intention receiver or brain-scanning device 12 is wearable and non-invasive. For example, in certain embodiments, device 12 may be incorporated into a user's hat, or other wearable head set, or may be inserted or worn over the ear. For example, device 12 may be an EEG, typically worn as a cap and including electrodes that pick up the electric fields produced by firing neurons.

In certain embodiments, brain-scanning device 12 includes multiple channels for detecting, receiving and interpreting a user's brain waves. For example, in some embodiments, brain-scanning device 12 includes at least two channels. In this embodiment, one of the at least two channels may detect brain waves attributable to a first dimension of directional intention (e.g., horizontal, or right and left), and the second channel of the at least two channels may detect brain waves attributable to a second dimension of directional intention different from the first (e.g., vertical, or up and down). In this manner, brain-scanning device 12 may be configured to distinguish a user's brain waves between two or more directional dimensions.

In certain embodiments of the present invention, movement or directional intention receiver or brain-scanning device 12 is a computing device separate from, but similar to, computing device 13, and may include, among other components, a memory 20 and processor 21 for analyzing the brain wave signals received from the user. That is, in certain embodiments, device 12 receives movements or brain waves (or signals corresponding to brain waves) from a user thinking directional thoughts, translates or converts, via processor 21 the movements or brain waves (or signals corresponding to brain waves) to directional or movement intentions, analyzes and interprets, via processor 21, the directional intentions as being up, down, left and/or right, transforms the directional intentions into a format usable by computing device 13, and outputs the directional intentions to computing device 13 for further processing. In this embodiment, once computing device 13 receives the directional intentions, processor 14 may interpret the directional intentions as a line pattern, search database 16 for a matching line pattern affiliated with a pre-defined operation, and send a command to device controller 18 of device 17 to perform the operation if and when a match occurs.

In an alternative embodiment, device 12 may output completed line patterns for further processing by computing device 13. In this embodiment, controller or processor 21 of device 12 may receive movement or brain wave signals, analyze the signals as a series of directional intentions, and analyze the directional intentions as a line pattern. Processor 21 may search a database stored in, for example, memory 20 for the specific line pattern. Once the line pattern is identified, processor 21 may send a command to device controller 18 of device 17 to perform the action, function or execution, or may record or output information corresponding to the line pattern, such as a character, numeral, word, or other item of information. In certain embodiments of the present invention, the identified line patterns may represent words, phrases or sentences that may for example be displayed on a display or output in another way or stored such as in memory 20. Device controller or processor 21 may be configured to carry out embodiments of the invention by, for example, executing software or code for example stored in memory 20.

In certain embodiments of the present invention, device 12 is an EEG device and a user may require training with the EEG, or other brain-scanning device, in order to effectively operate the device.

Figure 2:
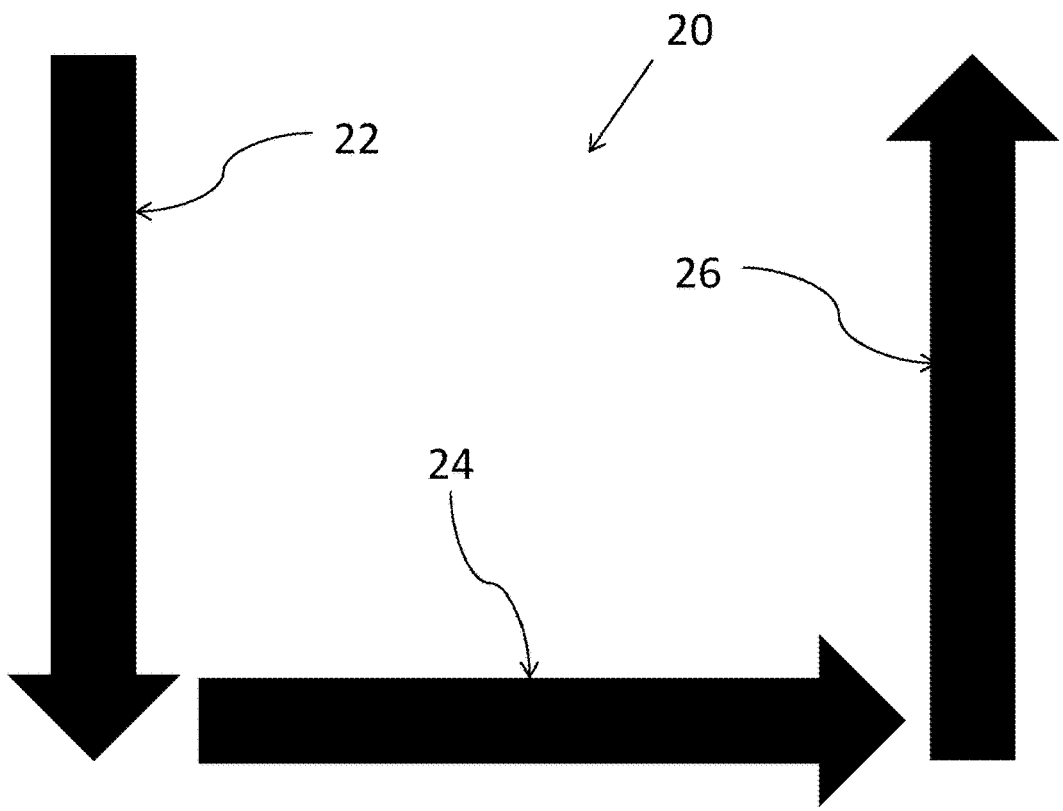
FIG. 2 is a schematic representation of a line pattern according to aspects of certain embodiments of the present invention.

Reference is now made to FIG. 2, which is a schematic representation of a line pattern 20 according to aspects of certain embodiments of the present invention. Line pattern 20 is not meant to be limiting in any way, and it is understood that many different combination of directional intentions are contemplated by the present invention.

As illustrated in FIG. 2, line patterns of the present invention may be defined by arrows so as to inform users how to pattern their thoughts in order to correctly perform the intended line pattern and execute the intended operation. In certain embodiments, a user may imagine a first movement or directional intention as "down", for example as if he/she was trying to telepathically move a ball lower on a computer screen, resulting in down directional intention 22. A user may then imagine a second directional intention as "right", as if he/she was trying to telepathically move a ball to the right on a computer screen, resulting in right directional intention 24. Next, a user may imagine a third directional intention as "up", as if he/she was trying to telepathically move a ball upwards on a computer screen, resulting in up directional intention 26. Down directional intention 22, right directional intention 24, and up directional intention 26 may together make up line pattern 20. Line pattern 20 may be pre-defined as being affiliated/associated with a specific operation, action, phrase, word, character, numeral, letter, or other item of information and stored on a database such as database 16. Brain-scanning device 12 may receive brain waves and may translate or convert the brain waves to directional intentions 22, 24 and 26 and output the directional intentions to computing device 13 where processor 14 interprets the directional intentions as line pattern 20, searches database 16 for the matching line pattern 20, and outputs or stores information such as a character or word or sends a command or control signal to device 17 or device controller 18 to perform/execute the pre-defined operation affiliated with line pattern 20 if and when a match occurs.

Figure 3:
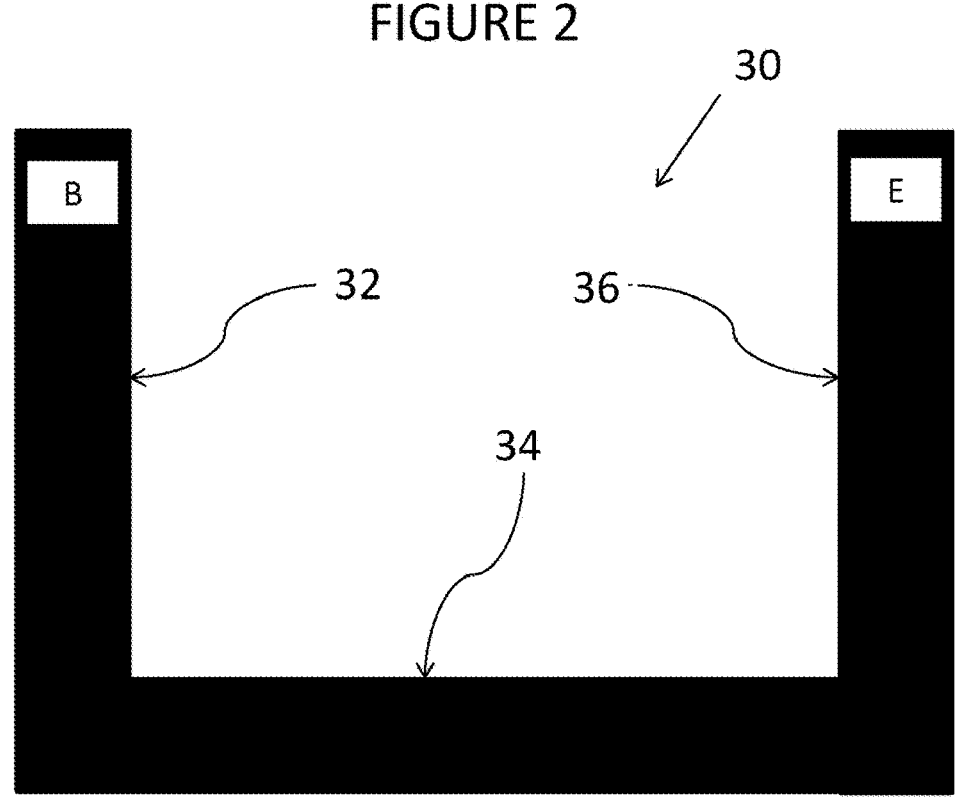
FIG. 3 is an alternative schematic representation of a line pattern according to aspects of certain embodiments of the present invention.

Reference is made to FIG. 3, which is an alternative schematic representation of a line pattern 30 according to aspects of certain embodiments of the present invention. In this representation, line pattern 30 is not represented by a series of arrows as is line pattern 20, but rather as a flow of directional thought starting at beginning B and stopping at ending E. As with line pattern 20, line pattern 30 includes a first directional thought as a down directional or movement intention 32, a second directional thought as a right directional thought 34, and a third directional thought as up directional intention 36.

In certain embodiments of the present invention, line patterns may include a plurality of steps. As used herein, a step is equivalent to a movement or directional intention, and a plurality of steps defines the directional intentions occurring between one beginning B and one ending E. For example, line pattern 30 includes three steps: beginning B; (1) down directional intention 32; (2) right directional intention 34; (3) up directional intention 36; and ending E. It is contemplated that line templates may include any number of steps occurring between a beginning B and an ending E, including, without limitation, a single step (e.g., a single directional intention) or a plurality of steps (e.g., two or more directional intentions).

Beginnings B and endings E may be defined in any number of different ways. For example, in certain embodiments, a beginning B may be triggered, for example, by a user pressing a button on device 12 or another device or computing device 13, and ending E may be triggered by the user pressing the same button again after cogitating, or affecting movement corresponding to, a series of directional intentions. In another embodiment, a beginning B may be triggered by the user pressing and holding the button and the ending E may be triggered by the user releasing the button. In another embodiment, a beginning B may be triggered by the user clenching his/her jaw and maintaining the jaw clench until ending E. In yet another embodiment, a beginning B may be defined as starting with the first directional intention cogitated by a user, and an ending E may be defined as a pause in cogitation of a pre-defined duration or time limit (e.g., at least one second or half of a second).

In the latter embodiment, a user may begin a line pattern by simply imagining the imagining a first directional or movement intention. The user may then continue to imagine any number of directional intentions in series until the system detects a pause in cogitation of pre-defined duration, at which time the system triggers an ending E to the series of directional intentions. At that time, the system may detect that the user has finished the line pattern and proceed to process the line pattern as discussed above. Alternatively, the user may begin a new part to the line pattern. That is, in certain embodiments, a line pattern may include two or more parts (e.g., a plurality of parts).

In another embodiment, a user may begin a line pattern by clenching his/her jaw and maintaining the jaw clench while imagining, or affecting movement corresponding to, a series of directional intentions. In some embodiments, the jaw clench may be a single jaw clench pulse or the jaw clench may be maintained. Other types of physiological triggers are contemplated such as, without limitation, an eye blink, smile or nod.

Figure 4:
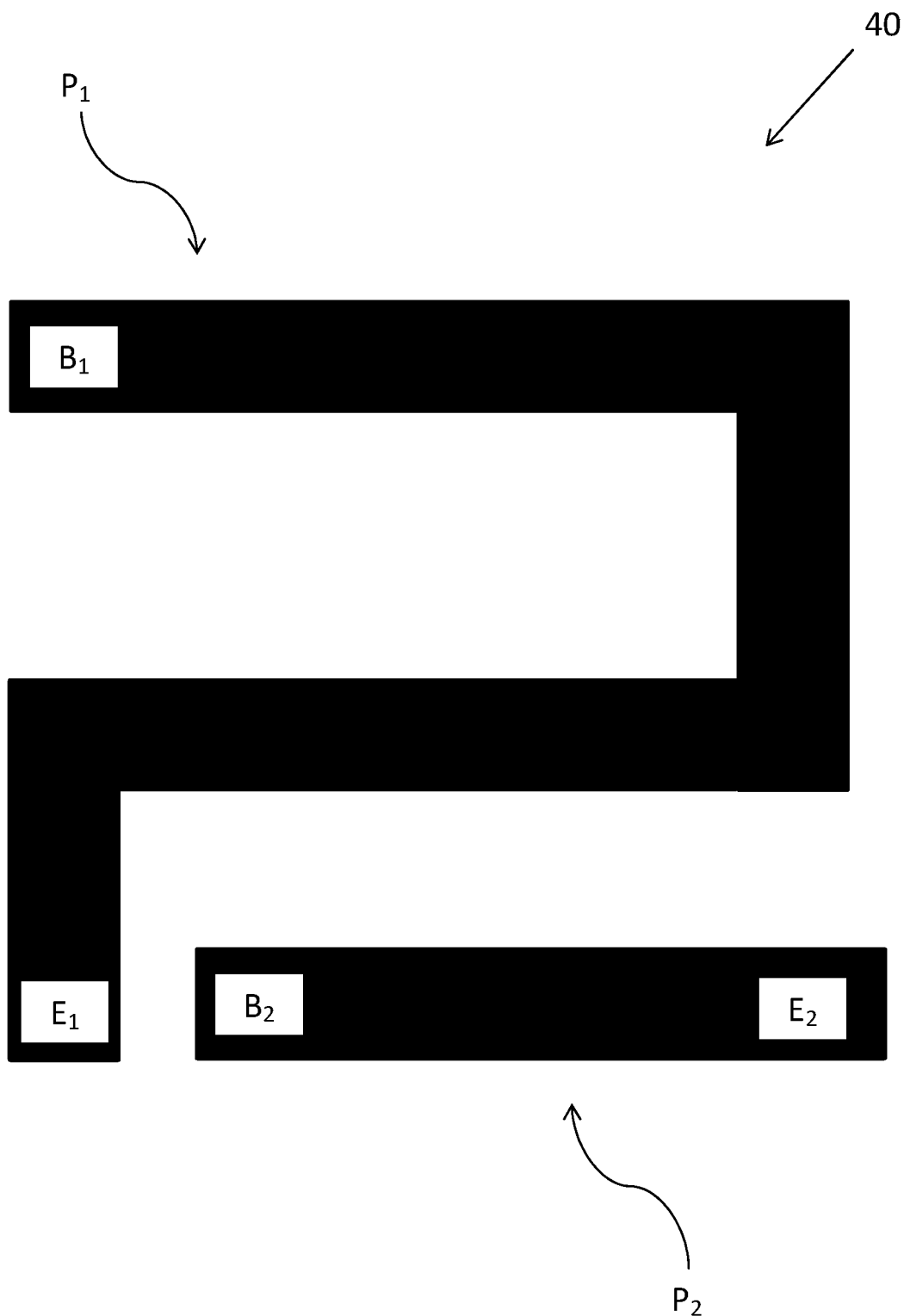
FIG. 4 is a schematic representation of line pattern including at least two parts according to aspects of certain embodiments of the present invention.

Reference is now made to FIG. 4, which is a schematic representation of line pattern 40, including at least two parts $P_1$ and $P_2$ according to aspects of certain embodiments of the present invention.

Multiple ways of initiating, triggering or beginning a rune or line pattern may be used. For example, a first beginning, initiation or triggering of a first part of a rune or line pattern may be based on a primer. Primers may include, without limitation, a moment of relaxation of a body part or a thought for a pre-defined duration followed by input coming in the form of the first movement or directional intention. Separation between parts of one rune, or separation between distinct runes may also include, without limitation, a moment of relaxation or pre-defined duration. Other primers exist. For example, a primer may include an eye blink, brow raise, jaw clench or smile which may be detected from micro gyroscopes, accelerometers, MEMS, infrared sensors or other movement-detecting technology. Additional primers may include, without limitation, pressing a button or key, flipping a switch, pushing a pressure switch (e.g., a pressure sensor) or any unique action that could put a non-tactile operating system into a "listening/reading" mode.

As discussed above, a user may begin a first part $P_1$ by initiating, or triggering, a first beginning $B_1$ by thinking a first directional thought, for example a right directional thought as illustrated in FIG. 4. Alternatively, the user may trigger first beginning $B_1$ by a movement or muscle movement for example blinking an eye, raising the brow, clenching the jaw, smiling, pressing a button, or flipping a switch. The user may continue to think a first series (or flow) of directional thoughts until the system detects a first ending $E_1$. First ending E.sub.1 may be, for example, a first pre-defined duration or time limit (e.g., one second or half of one second). Alternatively, first ending $E_1$ may be triggered by blinking an eye, raising the brow, clenching the jaw, smiling, pressing a button, or flipping a switch. Following the first ending $E_1$, which ends first part, section or segment $P_1$ of line pattern 40, the user may begin a second part $P_2$ by initiating, or triggering, a second beginning $B_2$ by thinking a subsequent directional thought, for example a second right directional thought as illustrated in FIG. 4. Alternatively, the user may trigger second beginning $B_2$ by blinking an eye, raising the brow, clenching the jaw, smiling, pressing a button, or flipping a switch. The user may continue to think a second series (or flow) of directional thoughts until the system detects a second ending $E_2$. In certain instances, $E_2$ may operate as the end of second part $P_2$, or, in other instances, $E_2$ may operate as the end of completed line pattern 40. In the former instance, $E_2$ may operate similar to $E_1$ and may be the first pre-defined duration, while in the latter instance $E_2$ may be a second pre-defined duration or time limit (e.g., two seconds). When the system detects that $E_2$ is the second pre-defined time limit, the system acknowledges that the line pattern has been completed and proceeds to process the line pattern as discussed above. Alternatively, second ending $E_2$ may be triggered by blinking an eye, raising the brow, clenching the jaw, smiling, pressing a button, or flipping a switch, each of which may be performed for a longer duration or multiple times to distinguish $E_2$ from $E_1$. Meta or control thoughts allowing for additional control include ending thoughts or durations, but may include other meta or control thoughts or durations.

Accordingly, in the embodiment as illustrated in FIG. 4, a user desires to create a line pattern including two parts, sections or segments, each part including one or more steps. The user triggers a first beginning $B_1$ of first part $P_1$ of the line pattern by thinking, in series, the directional intentions (e.g., steps) "right, down, left, and down" and waits the first pre-defined duration (e.g., one second) to trigger $E_1$ and the end of first part $P_1$. The user then triggers a second beginning B.sub.2 of second part $P_2$ by thinking the directional intention "right" and waits the second pre-defined duration (e.g., two seconds) to trigger $E_2$ and the end of the line pattern. As discussed above, beginnings B and endings E may also be triggered by blinking an eye, raising the brow, clenching the jaw, smiling, pressing a button, or flipping a switch.

Figure 5:
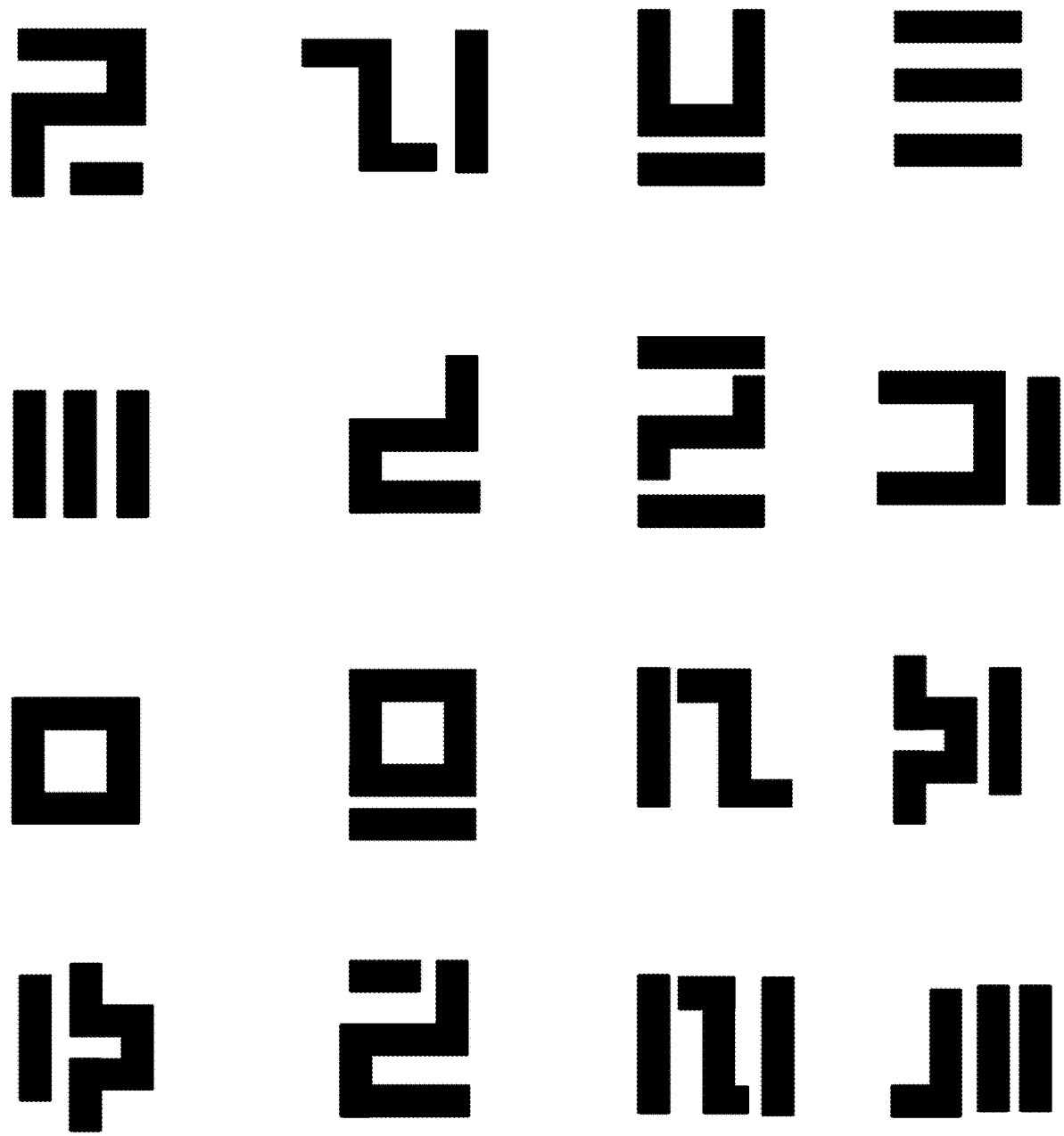
FIG. 5 is a table of various example line patterns according to certain embodiments of the present invention.

For illustration only, FIG. 5 is a table of various example line patterns having at least one part comprising one or more steps according to aspects of certain embodiments of the present invention. It is contemplated that the lines making up the line patterns illustrated in FIGS. 4 and 5 are single directional thoughts. In some embodiments, the lengths of these lines have no meaning and are merely graphical representations of the thoughts. In other embodiments, the lengths of the lines are representative of the depth of the directional intention, and the longer the line the longer the user is thinking the directional intention and vice versa. Each pattern in FIG. 5 may correspond to an item of information such as a command (e.g., start, stop, volume louder), a character, symbol, numeral, word, or meta-symbol. In some embodiments, series of line patterns may be strung together to form words, sentences, etc.

As noted above, $E_2$ may not trigger the completion of line pattern 40 and the user may again wait the first pre-defined duration at $E_2$ and trigger a third/subsequent beginning $B_n$ of a third/subsequent part $P_n$ by thinking a third/subsequent series of directional intentions until an ending $E_n$, which may be either an ending to the third/subsequent part $P_n$ or the ending to the line pattern.

Figure 6:
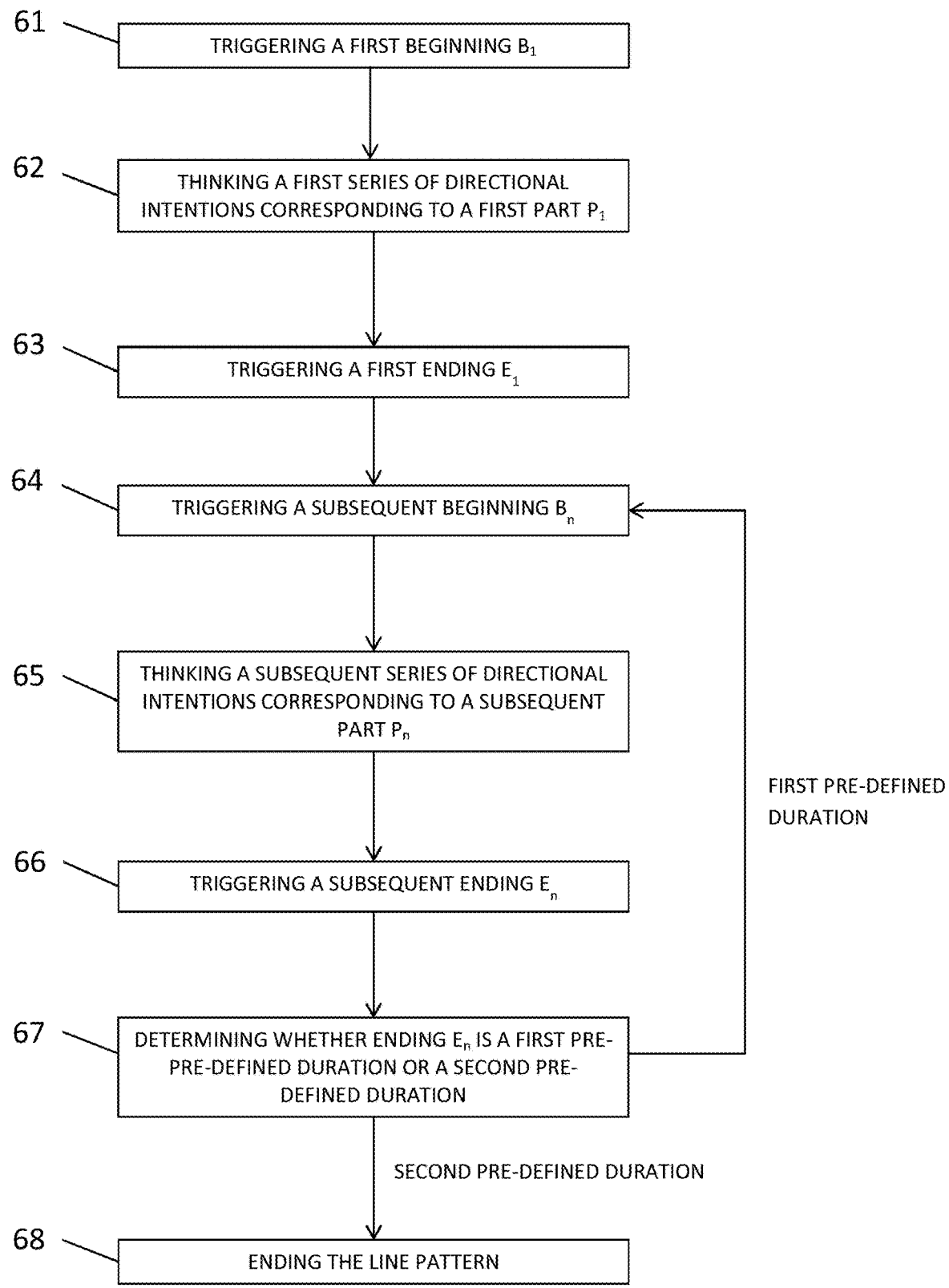
FIG. 6 is a flow chart of a method of producing a multi-part line pattern according to aspects of certain embodiments of the present invention.

Accordingly, FIG. 6 illustrates a flow chart of a method of producing a multi-part line pattern according to aspects of certain embodiments of the present invention. In certain embodiments, the method may include triggering, as discussed above, a first beginning $B_1$ (process 61), thinking a first series of steps corresponding to a first part $P_1$ (process 62) and thus receiving and interpreting brain waves corresponding to this, triggering, as discussed above, a first ending $E_1$ (process 63) by, for example, waiting a first pre-defined duration, blinking an eye, raising the brow, clenching the jaw, smiling pressing a button or flipping a switch, triggering, as discussed above, a subsequent beginning $B_2$ (process 64), thinking a subsequent series of directional intentions corresponding to a subsequent part $P_n$ (process 65) and thus receiving and interpreting brain waves corresponding to this, and triggering a subsequent ending $E_n$ (process 66). At process 67 it is determined whether ending $E_n$ is a first ending $E_1$ or a second ending $E_2$, as defined above. If ending $E_n$ is a first ending $E_1$, the method returns to process 64 wherein the user may trigger another beginning $B_n$ of another part $P_n$. If ending $E_n$ is a second ending $E_2$, the method continues to process 68 where the line pattern is completed and may be processed as described above.

Figure 7:
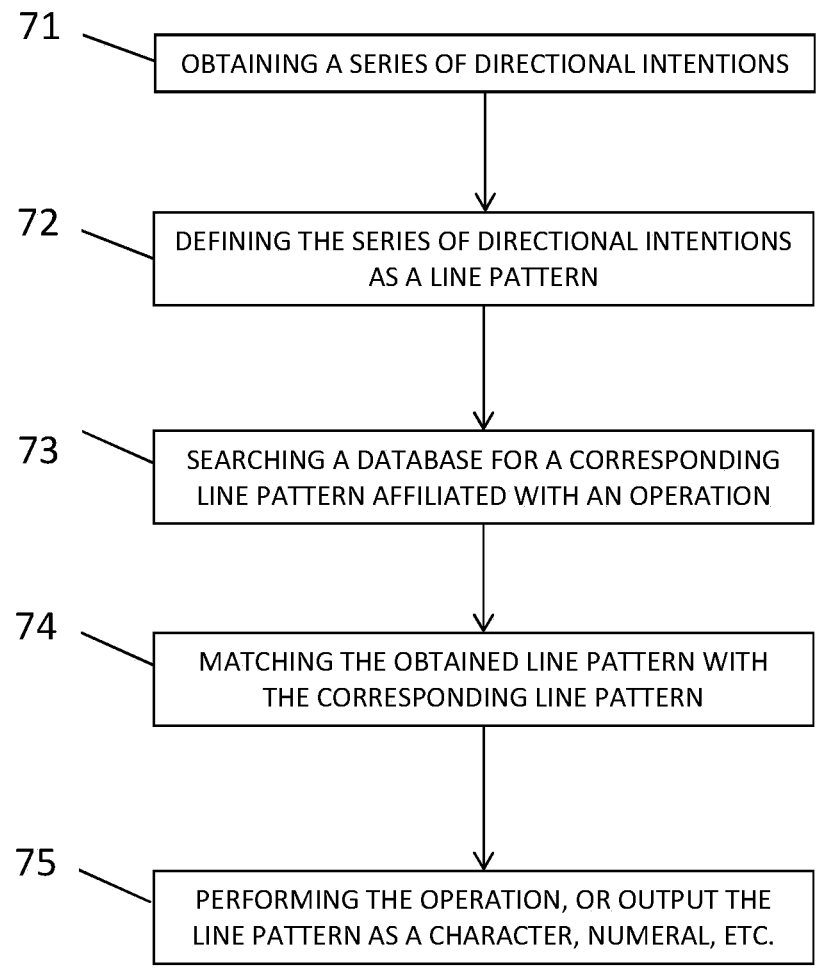
FIG. 7 is a flow chart of a method for controlling a device according to aspects of certain embodiments of the present invention.

Reference is now made to FIG. 7, which is a flow chart of a method for controlling a device according to aspects of certain embodiments of the present invention. As illustrated in FIG. 7, process 71 may include receiving or obtaining a series of directional or movement intentions from a user, or receiving signals corresponding to brain waves which correspond to directions or movements from a user and translating the signals or brain waves into directional or movement intentions. In preferred embodiments, the directional intentions may be obtained via brain-scanning device 12 receiving brain waves or signals that may be interpreted as directional intentions. The series of directional intentions may include any number of directional intentions, including one or more. As described above, it is contemplated that the series of directional intentions may include, without limitation, a plurality of steps and/or a plurality of parts. In some embodiments, each directional intention may include a depth.

In process 72, the series of directional intentions is defined as a distinct pattern or line pattern. In some embodiments, device 12 may define the pattern or line pattern and output the line pattern to computing device 13. In other embodiments, device 12 may receive signals corresponding to brain waves or movements and convert or interpret the brain waves or movements to directional or movement intentions, and output the series of directional or movement intentions, and computing device 13 may define the distinct line pattern. As indicated, the line pattern may include one or a plurality of parts, each part including at least one step or directional intention. In different embodiments, the functionality assigned to devices 12 and 13 may be assigned to other devices or the same device may receive brain wave signals, convert the signals, define the line patterns, and perform other functionality described herein.

After the line pattern obtained, or received, has been defined and output to computing device 13, a database (e.g., database 16) containing pre-defined line patterns is searched for the line pattern corresponding to the line pattern output to computing device 13 (process 73). Each corresponding line pattern in the database is associated or affiliated with a pre-determined character, numeral, or other informational item, or operation, action, process or execution. Once the corresponding line pattern is found, a match is made between the obtained line pattern and the corresponding line pattern that is affiliated with the information or operation (process 74). In this context, matching the line patterns may be equivalent to the system receiving a command or set of instructions. Upon a match occurring, the system is commanded to perform the operation affiliated with the corresponding line pattern (process 75), for example, by sending a control signal (e.g., an electrical signal, an infrared signal, etc.) to a device, or output the line pattern as a character, numeral, or other informational item.

In certain embodiments, the operation may be a simple command such as, without limitation, a command to turn a device on or off, or a command to type a particular letter of the alphabet. In other embodiments, the operation may be more complex such as typing a sentence or phrase, executing a software application, or performing a series of related commands. In yet another embodiment, the operation may correspond to a plaque, and the matching may command the system to perform each of the actions associated with the plaque, or to open the plaque database so that the user may choose an operation contained within the plaque.

As discussed above, in certain embodiments, brain-scanning device 12 includes multiple channels for detecting and interpreting a user's brain waves. For example, in some embodiments, brain-scanning device 12 includes at least two channels. In this embodiment, one of the at least two channels may detect brain waves attributable to a first dimension of directional intention (e.g., horizontal, or right and left), and the second channel of the at least two channels may detect brain waves attributable to a second dimension of directional intention different from the first (e.g., vertical, or up and down). In this manner, brain-scanning device 12 may be configured to distinguish a user's brain waves between two or more directional dimensions.

Accordingly, certain embodiments of the present invention feature a method for obtaining or receiving a series of directional intentions, or brain waves which correspond to directions or movements, comprising at least two directional dimensions, or dimensions of directional intentions (e.g., horizontal and vertical).

Figure 8:
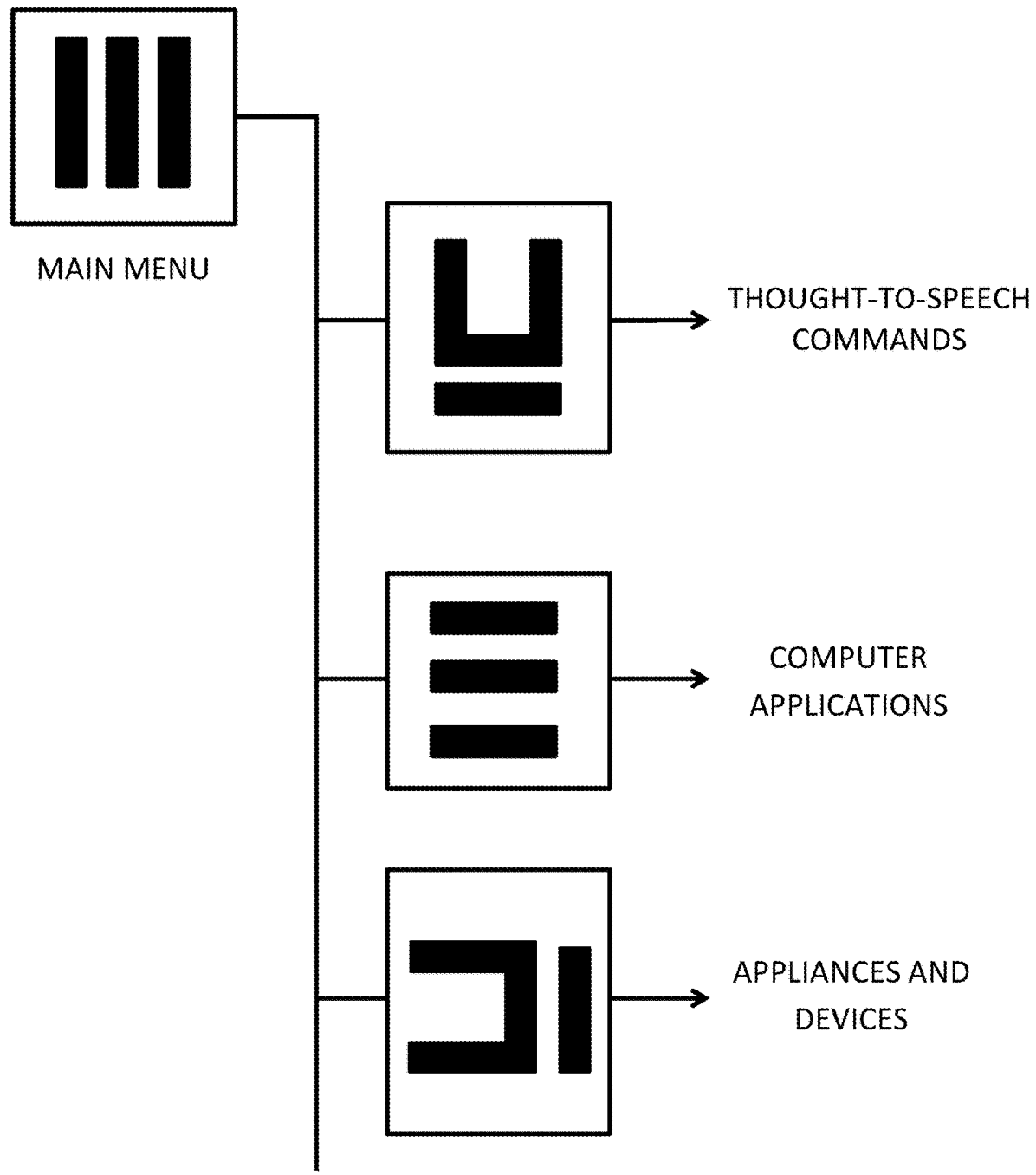
FIG. 8 is an illustration of a cognition user interface according to aspects of certain embodiments of the present invention.

Reference is now made to FIG. 8, which is an illustration of a CUI according to aspects of certain embodiments of the present invention. By executing a line pattern (e.g., rune) to get access to a new set of line patterns, users will be able to build their own menu systems and categories for common "executions" required in their daily routine. Line patterns may be organized in plaques such as thought-to-speech commands, computer applications, and appliances and devices as illustrated in FIG. 8.

Figure 9:
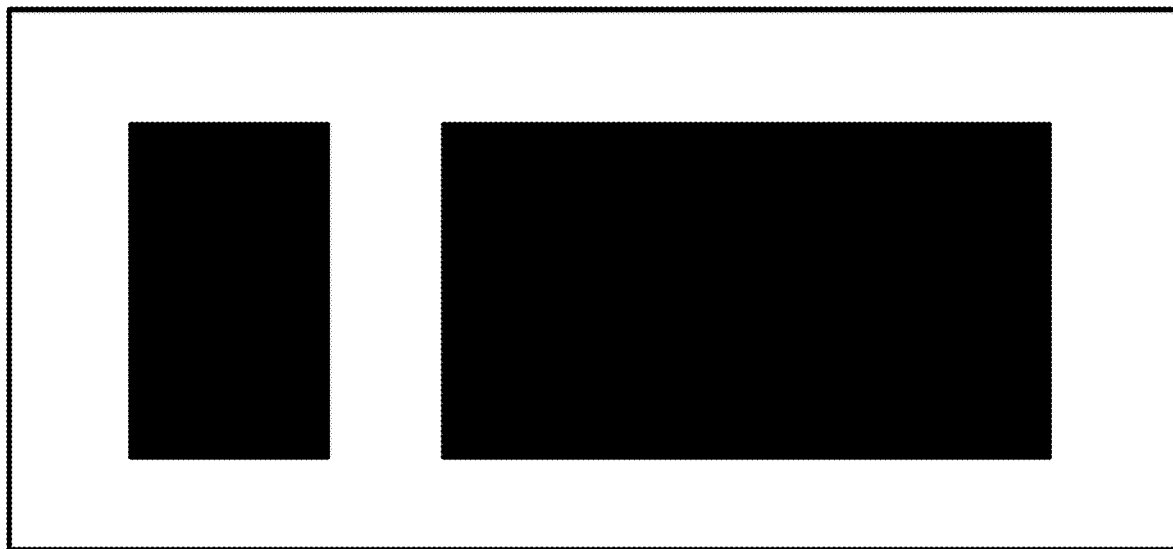
FIG. 9 is a graphical illustration of a series of pulses according to aspects of certain embodiments of the present invention.

Reference is now made to FIG. 9, which is a graphical illustration of a series of pulses according to aspects of certain embodiments of the present invention. In this embodiment, FIG. 9 illustrates one short pulse and one long pulse. However, it is contemplated that any number of pulses in any combination may be used.

As discussed above, a solution for the weaknesses of conventional one-to-one correlative thought control is the use of pulsed concentration in a series of short and long pulses (similar to Morse Code, but user/manufacturer defined) for the execution of nearly anything, including, without limitation: (1) thought-to-speech, where a series of pulses is associated to pre-defined words, phrases or numbers; (2) thought-to-control, where a series of pulses are associated to pre-defined actions or series of actions.

In order to convey this secondary solution, a pulse set can be defined as a collection of two or more pulses of concentration (e.g., short and/or long), that are combined in order to execute a single pre-defined action (or set of actions) or to speak a word, sentence or pre-defined paragraph. The length of time for a short and long pulse can be user-defined or manufacturer-defined. In this way, a pulse set may be utilized in a similar manner as line patterns described above. Pulses of concentration may include for example detection of or input via jaw clenches or eye blinks. Numbers of pulses other than two may be used.

In certain embodiments, a pulse set may be associated with pre-defined words, phrases or numbers. In another or the same embodiment, a pulse set may be associated with pre-defined actions or a series of actions.

While certain features of the present invention have been illustrated and described herein, many modifications, substitutions, changes, and equivalents may occur to those of ordinary skill in the art. It is, therefore, to be understood that the appended claims are intended to cover all such modifications and changes as fall with the true spirit of the invention.

The invention claimed is:

1. A system for controlling operation of a device comprising:
   an earbud comprising:
      one or more sensors for recording actions performed by a user of the earbud;
      a processor communicatively coupled to the one or more sensors, wherein the processor is configured to:
         identify, via the one or more sensors, when the user has performed a primer,
         in response to identifying the primer, identifying, via the one or more sensors, a line pattern performed by the user after the performance of the primer, wherein the line pattern comprises a plurality of segments forming a three-dimensional pattern, and
         transmits the line pattern to a second device; and
      the second device comprising:
         a second processor for executing one or more instructions stored on a memory coupled to the second processor to output a control signal based at least in apart on the transmitted line pattern.

2. The system of claim 1, comprising:
   a third device comprising a controller, wherein the third device receives the control signal from the second device.

3. The system of claim 1, comprising:
   a third device comprising a display, wherein the third device receives the control signal from the second device.

4. The system of claim 1, wherein the earbud comprises at least one of electroencephalography (EEG) devices, movement receivers, micro gyroscopes, accelerometers, microelectromechanical systems (MEMS), motion-detecting infrared sensors, magnetic resonance imaging (MRI) devices, nuclear magnetic resonance imaging (NMRI) devices, magnetic resonance tomography (MRT) devices, or magnetoencephalography (MEG) devices.

5. The system of claim 1, wherein the primer comprises at least one of a head nod, a head tilt, a relaxation of a body part, an eye blink, a brow raise, a jaw clench, or a smile.

6. The system of claim 1, wherein the line pattern is one of a series of line patterns.

7. The system of claim 1, wherein the line pattern represents at least one of a symbol, letter, numeral, character, glyph, icon, sign, and rule.

8. The system of claim 1, wherein the second device outputs a control signal by matching the transmitted line pattern with a stored line pattern in a database of the second device.

9. The system of claim 5, wherein the primer comprises at least one of a long jaw clench, a short jaw clench, or a combination thereof.

10. The system of claim 1, wherein the plurality of segments are selected from the group consisting of up, down, left, right, forward, or backward.

11. A method for controlling operation of a third device comprising:
    receiving, from an earbud at a second device, signals corresponding to actions performed by a user of the earbud;
    identifying, at the second device, when the user has performed a primer based on the signals;
    in response to identifying the primer, identifying, at the second device, a line pattern performed by the user after the performance of the primer, wherein the line pattern comprises a plurality of segments forming a three-dimensional pattern;
    generating, at the second device, a control signal based at least in part on the identified line patterns; and
    outputting, from the second device, the control signal to the earbud or a third device, wherein the control signal is related to a pre-defined action.

12. The method of claim 11, wherein generating the control signal comprises matching at least one of the generated line patterns with a pre-defined line pattern stored in a database of the second device.

13. The method of claim 11, comprising:
    modifying the operation of the third device based on the control signal.

14. The method of claim 11, wherein the received signals are recorded across a plurality of channels of the earbud.

15. The method of claim 11, wherein the primer comprises at least one of a head nod, a head tilt, a relaxation of a body part, a brow raise, a smile, an eye blink, and a jaw clench.

16. The method of claim 15, comprising:
    detecting the jaw clench by at least one of:
       determining a change in an inner ear pressure of the user of the earbud; and
       detecting electrical activity due to muscle movement.

17. The method of claim 11, wherein identifying the line pattern comprises:
    determining a length for each line segment within the line pattern.

18. The method of claim 11, wherein the line pattern comprises a selection of short and long pulses.

19. The method of claim 15, wherein the primer comprises at least one of a long jaw clench, a short jaw clench, or a combination thereof.

20. The method of claim 11, wherein the plurality of segments are selected from the group consisting of up, down, left, right, forward, or backward.

* * * * *